United States Patent [19]

Tomisawa et al.

[11] Patent Number: 4,600,540

[45] Date of Patent: Jul. 15, 1986

[54] BENZOYLPROPIONIC ACID DERIVATIVES

[75] Inventors: Kazuyuki Tomisawa, Saitama; Kazuya Kameo; Toru Matsunaga, both of Ageo; Shiuji Saito, Niiza; Kaoru Sota, Tokorozawa, all of Japan

[73] Assignee: Taisho Pharmaceutical Co., Ltd., Tokyo, Japan

[21] Appl. No.: 741,127

[22] Filed: Jun. 4, 1985

[30] Foreign Application Priority Data

Jun. 5, 1984 [JP] Japan ................ 59-114887

[51] Int. Cl.⁴ .................... C07C 153/023
[52] U.S. Cl. .................... 558/255
[58] Field of Search ............ 260/455 R; 514/513

[56] References Cited

U.S. PATENT DOCUMENTS 3,598,854 10/1971 Steinberg ............ 260/455 R

Primary Examiner—Henry R. Jiles
Assistant Examiner—Robert C. Whittenbaugh

Attorney, Agent, or Firm—Cushman, Darby & Cushman

[57] ABSTRACT

Benzoylpropionic acid derivatives represented by the general formula

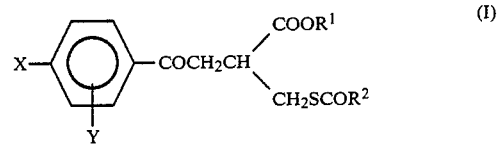

(wherein $R^1$ represents a hydrogen atom, a lower alkyl group or a benzyl group, $R^2$ represents a lower alkyl group or a phenyl group, X represents a hydrogen atom, a halogen atom, a lower alkyl group, a lower alkoxy group, a phenoxy group or a halogenophenoxy group, and Y represents a hydrogen atom or a lower alkyl group). The compounds have immunomodulative function and are effective for treatment of diseases caused by abnormal immunofunction.

6 Claims, No Drawings

BENZOYLPROPIONIC ACID DERIVATIVES

BACKGROUND OF THE INVENTION

The present invention relates to novel benzoylpropionic acid derivatives, and more particularly, it relates to 2-acylthiomethyl-3-benzoylpropionic acid derivatives which have immunomodulative function and are effective for treatment of diseases caused by abnormal immunofunction.

In the past, there have been used the so-called immunosuppressors for treatment of autoimmune diseases such as chronic rheumatoid arthritis. In general, however, the suppressive activity of the agents is mainly based on cytotoxicity. Accordingly, because of a strong side-effect depending on the above-mentioned cytotoxicity, these agents can not be said to be appropriate as therapeutical agents of autoimmune diseases which are required to be administered continuously for a long term.

Further, in order to treat diseases related to immune, there have been recently used the so-called immunomodulators which have the effect to regulate the immune function, i.e., either stimulate the immune function when lowered, or suppress the immune function when augmented. However, even these agents can not be said to be satisfactory in aspects of effect, side-effect and toxicity.

As a result of the earnest studies, the present inventors have found that certain 2-acylthiomethyl-3-benzoylpropionic acid deivatives have good immunomodulative function, weak side-effect and weak toxicity, and thus the present invention has been completed.

SUMMARY OF THE INVENTION

An object of the present invention is to provide novel 2-acylthiomethyl-3-benzoylpropionic acid derivatives which have immunomodulative function and are effective for treatment of diseases caused by abnormal immunofunction and the process for producing them.

Other objects and advantages of the present invention will be apparent from the following descriptions.

DETAILED DESCRIPTION OF THE INVENTION

The present invention is illustrated in detail hereunder.

The objective compound of the present invention is a 2-acylthiomethyl-3-benzoylpropionic acid derivative (hereinafter referred to as Compound I) having the general formula

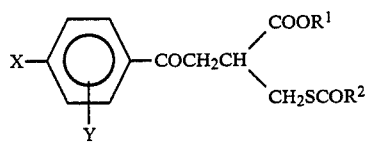

(I)

(wherein $R^1$ represents a hydrogen atom, a lower alkyl group or a benzyl group, $R^2$ represents a lower alkyl group or a phenyl group, X represents a hydrogen atom, a halogen atom, a lower alkyl group, a lower alkoxy group, a phenoxy group or a halogenophenoxy group, and Y represents a hydrogen atom or a lower alkyl group).

The halogen atom, herein, for X is a fluorine, chlorine or bromine atom, and the lower alkyl group for $R^1$, $R^2$, X and Y is a straight or branched chain alkyl group having up to 5 carbon atoms. The lower alkoxy group for X is one having up to 3 carbon atoms, and the halogenophenoxy group for X is a chlorophenoxy group, a bromophenoxy group and the like.

The preferred objective compounds are the compounds of formula I wherein $R^1$ is a hydrogen atom, $R^2$ is a methyl group, X is a hydrogen atom, a bromine atom or a methyl group and Y is a hydrogen atom or a methyl group.

The compound I can be prepared, for example, by the following method.

(1) A carboxylic acid compound (hereinafter referred to as Compound II) represented by the general formula

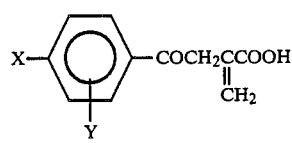

(II)

(wherein X and Y are as defined above) is dissolved in an organic solvent (e.g., methanol, ethanol, acetone, dimethylformamide, hexamethylphosphoric triamide, dimethyl sulfoxide and the like), and a thiocarboxylic acid represented by the general formula $R^2COSH$ (wherein $R^2$ is as defined above) is added in an amount of 1–2 equivalents relative to the compound II. The mixture is reacted in the presence of 0.01–0.1 equivalent of a basic catalyst (e.g., sodium carbonate, potassium carbonate, lithium carbonate, sodium hydrogencarbonate, potassium hydrogencarbonate and the like) at $-20°$ to $50°$ C. for 0.5 to 24 hours to give the compound I of the carboxylic acid type (the compound of formula I wherein $R^1$ is hydrogen atom).

(2) The compound I of the carboxylic acid type as obtained in the item (1) is reacted with a conventional alkylating or benzylating agent having the alkyl or benzyl group for $R^1$ of formula I (e.g., an alkyl halide, a dialkyl sulfate, benzyl halide and the like) in the presence of a base (e.g., sodium carbonate, potassium carbonate, lithium carbonate, sodium hydrogencarbonate, potassium hydrogencarbonate, sodium hydroxide, potassium hydroxide, sodium hydride, a sodium alkoxide and the like) in an organic solvent (e.g., acetone, dimethylformamide, hexamethylphosphoric triamide, dimethyl sulfoxide and the like) to give the compound I of the ester type (the compound of formula I wherein $R^1$ is a lower alkyl group or a benzyl group).

The compound II of the starting material may be prepared, for example, according to the method of R. E. Lutz et al [Journal of American Chemical Society, Vol. 75, page 5039 (1953)], or may be prepared by Friedel-Crafts reaction of a benzene derivative (hereinafter referred to as Compound III) represented by the general formula

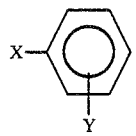

(III)

(wherein X and Y are as defined above) with itaconic anhydride according to the method similar to that described above.

The compounds I have a good imunomodulative function, low side-effect and low toxicity, therefore they are useful therapeutical agents of the diseases caused by abnormal immunofunction, for example, rheumatoid arthritis, autoimmune diseases, cancer, bacterial infectious diseases, asthma and the like. For the purposes, the compound of the present invention may be administered orally or parenterally in a conventional dosage form such as tablets, capsules, powders, granules, syrup and injectional forms prepared according to conventional pharmaceutical practices.

The effective dosage of the compound of the present invention depends on the age, weight or response of the patient. Generally, however, the daily dosage in adults may range from 0.1 to 3 g, preferably 0.3 to 1.5 g in single or divided doses.

The effect of the compound I is illustrated below by Experiments.

EXPERIMENT 1

Effect on adjuvant arthritis is Sprague-Dawley rats (chronic rheumatoid arthritis model)

10 Female Sprague-Dawley rats, 8 weeks old, weighting 160-190 g were used per each group. Rats of each group were administered subcutaneously into the tail with a suspension of 0.6 mg of heated killed mycobaterium butyricum in liquid parafin. Each of the compounds I, suspended in a 5% gum arabic solution, was administered orally once a day to rats of different groups in different amounts after sensitization.

At intervals were measured the edema volume of the hind paw of rats in the drug-treated groups and the control (drug-untreated groups) for evaluating tumor suppression activity of the compounds I.

Table 1 shows the results at 21 days after sensitization.

TABLE 1

| Drug | Dose (mg/kg) | Edema volume (ml) | Tumor suppression rate (%) |
|---|---|---|---|
| 1 | 30 | 0.58 ± 0.18* | 69.0 |
| 4 | 30 | 0.64 ± 0.29* | 65.8 |
|   | 100 | 0.36 ± 0.14** | 80.7 |
|   | 300 | 0.12 ± 0.09** | 93.6 |
| Control | 0 | 1.87 ± 0.48 | 0 |

Note
(1) Drug number means one of the compounds I which is prepared in the following Example attached the same number of Example as that of the drug in Table.
(2)*: significant at $p < 0.05$ by T-test
**: significant at $p < 0.01$ by T-test It is recognized from the above results that the compounds I suppress strongly the adjuvant arthritis in Sprague-Dawley rats and possess immunomodulative and antiarthritic activities

EXPERIMENT 2

Effect on adjuvant arthritis in Lewis rats (Cellular immunostimulation)

10 Female Lewis rats, 9 weeks old, weighing 180-190 g were used per each group. Rats of each group were administered subcutaneously into the tail with a suspension of 0.6 mg of heated killed mycobaterium butyricum in liquid parafin. Each of the compounds I, suspended in a 5% gum arabic solution, was administered orally once a day to rats of different groups in an amounts of 100 mg/Kg after sensitization. As a comparative drug was used D-penicillamine in the form of an aqueous solution, which was administered orally to rats of different groups in a manner similar to the compound I.

In intervals were measured the edema volume of the hind paw of rats in the drug-treated groups and the control (the drug-untreated groups) for evaluating the tumor stimulating activity of the drug.

Table 2 shows the results at 21 days after sensitization.

TABLE 2

| Drug | Edema volume (ml) | Tumor stimulating ratio |
|---|---|---|
| 2 | 3.46 ± 0.47 | 1.27 |
| 3 | 3.22 ± 0.09* | 1.18 |
| 4 | 3.27 ± 0.28 | 1.20 |
| 7 | 3.41 ± 0.19** | 1.25 |
| 13 | 3.63 ± 0.11** | 1.33 |
| 16 | 3.18 ± 0.17* | 1.17 |
| D-penicillamine | 3.76 ± 0.11** | 1.38 |
| control | 2.72 ± 0.13 | 1.00 |

Note
(1) Drug number means one of the compounds I which is prepared in the following Example attached the same number of Example as that the drug in Table.
(2)*: significant at $p < 0.05$ by T-test
**: significant at $p < 0.01$ by T-test It is recognized from the above results that the compounds I stimulate the adjuvant arthritis in Lewis rats and possess cellular immunostimulating activity as well as D-penicillamine.

EXPERIMENT 3

Effect on delayed-type footpad reaction (Cellular immunomodulating effect)

8 Female Balb/c mice, 8-12 weeks oil, weighing 20-24 g were used per each group. Mice of each group were administered subcutaneously into the right footpad with $1 \times 10^8$ sheep red blood cells as antigen to be sensitized.

Each of the compounds I, suspended in a 0.5% gum arabic saline solution, was administered intraperitoneally to mice of different groups in different amounts 2 hours after the sensitization.

Four days after the sensitization, mice of each group were administered subcutaneously into the left footpad with $1 \times 10^8$ sheep red blood cells, and the increase of thickness of swelling footpad was measured for evaluating the suppression to the delayed-type footpad reaction according to the method of Lagrange et al [Journal of Experimental Medicine, vol. 139, page 528,(1974)].

The results are shown in Table 3.

TABLE 3

| Drug | Dose (mg/kg) | Increase of thickness of swelling footpad ($\times 10^{-2}$ mm) | Suppression rate of delayed-type footpad reaction |
|---|---|---|---|
| 1 | 0 | 164.4 ± 9.1 | 0 |
|   | 10 | 102.5 ± 10.8** | 37.7 |
|   | 100 | 80.6 ± 8.0** | 51.0 |
| 4 | 0 | 126.4 ± 6.1 | 0 |
|   | 10 | 115.6 ± 4.8 | 8.5 |
|   | 100 | 89.4 ± 5.5** | 29.3 |

(Note)
(1) Drug number means one of the compounds I which is prepared in the following Example attached the same number of Example as that of the drug in Table.
(2)**: significant at p < 0.01 by T-test.

It is recognized from the above results that the compounds I suppress the delayed-type footpad reaction and have the cellular immunomodulating effect.

EXPERIMENT 4

Stimulating effect of lymphocytes transformation (Immunomodulative stimulating effect)

Mediums of RPMI-1640 (produced by GIBCO Co.) containing the compound I only (A medium), and containing a mitogen (lipopolysaccharide 0.2 μg/ml) and the compound I (B medium) were prepared.

$2 \times 10^5$ of spleen lymphocytes of female $BDF_1$ mice, 8–12 weeks old, weighing 20–22 g were cultured on each of the mediums at 37° C. for 48 hours under a 5% carbon dioxide in air. 0.25 μCi of $^3$H-thymidine was added to each of the mediums, and cultivation was further carried out for 22 hours. After completion of the cultivation, the lymphocytes were collected and their radio activity was measured to calculate the $^3$H-thymidine uptake into the lymphocytes for evaluating mitogenation.

The results were expressed as percent to $^3$H-thymidine uptake into lymphocytes in the control medium (not containing the compound I) and shown in Table 4.

TABLE 4

| Drug | Drug concentration (μg/ml) | $^3$H—thimidine uptake (% of control) A medium | B medium |
|---|---|---|---|
| 1 | 0.3 | 120 | 134** |
|   | 1 | 114 | 146** |
|   | 3 | 129 | 177** |
|   | 10 | 128 | 217** |
|   | 30 | 149* | 241** |
| 4 | 0.3 | 83 | 115 |
|   | 3 | 97 | 107 |
|   | 30 | 117 | 131** |
| control | 0 | 100 | 100 |

(Note)
(1) Drug number means one of the compounds which is prepared in the following Example attached the same number of Example as that of the drug in Table.
(2)*: significant at p < 0.05 by T-test.
**: significant at p < 0.01 by T-test.

It is recognized from the above results that the compounds I stimulate the mitogenation of spleen lymphocytes of mice by lipopolysaccharide and have immunomodulative simulating effect.

EXPERIMENT 5

Acute toxicity 7 male, 7 weeks old, Wister rats weighing 149–160 g were used per each for test. Rats were administered orally with a suspension of the compound I of Example 1 in a 5% gum arabic solution and observed for 7 days after administration, and the $LD_{50}$ value was calculated. The $LD_{50}$ value were excess of 1200 mg/kg.

The present invention is concretely illustrated bellow by Referential Examples and Examples.

REFERENTIAL EXAMPLE 1

In 150 ml of methylene chloride were dissolved 35.0 g of toluene and 22.4 g of itaconic anhydride. To this was added gradually 50.0 g of anhydrous aluminum chloride under ice-cooling with stirring, and then the mixture was stirred at room temperature for 5 hours for proceeding the reaction. After completion of the reaction, the reaction solution was concentrated under reduced pressure, poured into a mixture of 40 ml of conc. hydrochloric acid and 500 g of ice, and extracted with ethyl acetate. The extract was washed with water and dried over magnesium sulfate. The solvent was evaporated and the residue was recrystallized from a mixture of hexane and ethyl acetate to give 21.6 g of 3-(4-methylbenzoyl)-2-methylenepropionic acid (a compound of formula II wherein X is $CH_3$ and Y is H) (yield: 53%)
m.p. 137°–138° C.

REFERENTIAL EXAMPLE 2

Following the procedure of Referential Example 1 using the corresponding compounds III, there were obtained the compounds of formula II wherein X is $(CH_3)_2CH$ and Y is H (m.p. 144°–146° C., yield: 51%), X is $CH_3O$ and Y is H (m.p. 138°–140° C., yield: 44%), X is p-$ClC_6H_4O$ and Y is H (m.p. 144°–145° C., yield: 44%), X is $CH_3$ and Y is 2-$CH_3$ (m.p. 108.5°–109.5° C., yield: 12%) and X is $CH_3$ and Y is 3-$CH_3$ (m.p. 144°–146° C., yield: 33%)

EXAMPLE 1

To a solution of 19.0 g of 3-benzoyl-2-methylenepropionic acid in 30 ml of dimethylformamide was added 8.0 ml of thioacetic acid. 2.5 ml of a 30% aqueous potassium carbonate solution was added dropwise at room temperature over 30 minutes with stirring, and the mixture was stirred at room temperature for further 30 minutes for proceeding the reaction. After completion of the reaction, ice-water was added to the reaction solution, and the solution was neutralized with dil. hydrochloric acid, and extracted with ethyl acetate. The organic layer was washed with water and dried over magnesium sulfate. The ethyl acetate was evaporated under reduced pressure, and the residue was purified by a silica gel column chromatography (Wako gel C-200, produced by Wako Junyaku Co., a mixture of hexane and chloroform as a developing solvent) and recrystallized from a mixture of hexane and ethyl acetate to give 24.5 g of 2-acethylthiomethyl-3-benzoylpropionic acid as crystals (yield: 92%).
m.p. 100°–101° C.

Elementary analysis for $C_{13}H_{14}O_4S$. Calcd. (%): C 58.63; H 5.30. Found (%): C 58.67; H 5.31.

EXAMPLES 2–11

Following the procedure of Example 1 using the corresponding compounds II, there were obtained the following compounds I.

General formula

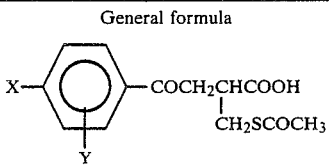

(I)

|  |  |  | Compound II | Compound I m.p. | yield |
|---|---|---|---|---|---|
| Example | X | Y | m.p. (°C.) | (°C.) | (%) |
| 2 | F | H | 108–109 | 106.5–108 | 75 |
| 3 | Cl | H | 180–181 | 109.5–110 | 66 |
| 4 | Br | H | 146.5–149 | 126.5–128 | 82 |
| 5 | $CH_3$ | H | 137–138 | 94–95.5 | 53 |
| 6 | $(CH_3)_2CH$ | H | 144–146 | 78–79 | 71 |
| 7 | $CH_3O$ | H | 138–140 | 88–90 | 62 |
| 8 | $C_6H_5O$ | H | 149–151 | 92–92.5 | 80 |
| 9 | p-$ClC_6H_4O$ | H | 144–145 | 108–110 | 30 |
| 10 | $CH_3$ | 2-$CH_3$ | 108.5–109.5 | 76–77.5 | 60 |
| 11 | $CH_3$ | 3-$CH_3$ | 144–146 | 111–113 | 69 |

EXAMPLE 12

Following the procedure of Example 1 using 10 ml of thiopropionic acid in place of 8.0 ml of thioacetic acid, there was obtained 19.0 g (yield: 68%) of 3-benzoyl-2-propionylthiomethylpropionic acid as crystals.

m.p. 76°–78° C.

Elementary analysis for $C_{14}H_{16}O_4S$. Calcd. (%): C 59.98; H 5.75. Found (%): C 60.21; H 5.69.

EXAMPLE 13

Following the procedure of Example 1 using 16.5 g of thiobenzoic acid in place of 8.0 ml of thioacetic acid, there was obtained 11.2 g (yield: 34%) of 3-benzoyl-2-benzoylthiomethylpropionic acid as crystals.

m.p. 110°–111° C.

Elementary analysis for $C_{18}H_{16}O_4S$. Calcd. (%): C 65.84; H 4.91. Found (%): C 66.12; H 5.07.

EXAMPLE 14

Following the procedure of Example 1 using 26.9 g of 3-(4-bromobenzoyl)-2-methylenepropionic acid and 10 ml of thiopropionic acid in place of 19.0 g of 3-benzoyl-2-methylenepropionic acid and 8.0 ml of thioacetic acid, respectively, there was obtained 25.5 g (yield: 71%) of 3-(4-bromobenzoyl)-2-propionylthiomethylpropionic acid as crystals.

m.p. 122.5°–123° C.

Elementary analysis for $C_{14}H_{15}BrO_4S$. Calcd. (%): C 46.81; H 4.21. Found (%): C 46.77; H 4.37.

EXAMPLE 15

Following the procedure of Example 4 using 16.5 g of thiobenzoic acid in place of 10 ml of thiopropionic acid, there was obtained 14.7 g (yield: 36%) of 3-(4-bromobenzoyl)-2-benzoylthiomethylpropionic acid as crystals.

m.p. 133°–135° C.

Elementary analysis for $C_{18}H_{15}BrO_4S$. Calcd. (%): C 53.08; H 3.71. Found (%): C 53.11; H 3.87.

EXAMPLE 16

To a solution of 26.6 g of 2-acetylthiomethyl-3-benzoylpropionic acid in 200 ml of dimethylformamide were added 15.6 g of diethyl sulfate and 14.0 g of potassium carbonate, and the mixture was stirred at room temperature for 3 hours for proceeding the reaction.

After completion of the reaction, ice-water was added to the reaction solution, and the mixture was extracted with diethyl ether. The organic layer was washed with water and dried over magnesium sulfate. The diethyl ether was evaporated under reduced pressure and the residue was purified by a silica gel column chromatography (Wako gel C-200 produced by Wako Junyaku Co.; a mixture of hexane and diethyl ether as a developing solvent) to give 22.1 g (yield: 75%) of ethyl 2-acethylthiomethyl-3-benzoylpropionate as a colorless oil.

NMR (CDCl$_3$), ppm 1.27 (3H, t, J=7 Hz); 2.36 (3H, s), 3.12–3.60 (5H, m); 4.19 (2H, q, J=7 Hz), 7.52 (3H, m); 7.98 (2H, d, J=8 Hz).

Elementary analysis for $C_{15}H_{18}O_4S$. Calcd. (%): C 61.20; H 6.16. Found (%): C 61.10; H 6.13.

EXAMPLE 17

Following the procedure of Example 16 using 34.5 g of 2-acetylthiomethyl-3-(4-bromobenzoyl)propionic acid and 12.8 g of dimethyl sulfate in place of 26.6 g of 2-acetylthiomethyl-3-benzoylpropionic acid and 15.6 g of diethyl sulfate, respectively, there was obtained 34.8 g (yield: 97%) of methyl 2-acetylthiomethyl-3-(4-bromobenzoyl)propionate as a colorless oil.

NMR (CDCl$_3$), ppm 2.33 (3H, s), 3.07–3.56 (5H, m); 3.71 (3H, s); 7.62 (2H, d, J=8 Hz) 7.82 (2H, d, J=8 Hz).

Elementary analysis for $C_{14}H_{15}BrO_4S$. Calcd. (%): C 46.81, H 4.21. Found (%): C 46.53; H 4.16.

EXAMPLE 18

Following the procedure of Example 17 using 15.6 g of diethyl sulfate in place of 12.8 g of dimethyl sulfate, there was obtained 27.2 (yield: 73%) of ethyl 2-acetylthiomethyl-3-(4-bromobenzoyl)propionate as a colorless oil.

NMR (CDCl$_3$), ppm 1.26 (3H, t, J=7 Hz); 2.35 (3H, s); 3.06–3.54 (5H, m); 4.18 (2H, q, J=7 Hz); 7.62 (2H, d, J=8 Hz); 7.83 (2H, d, J=8 Hz).

Elementary analysis for $C_{15}H_{17}BrO_4S$. Calcd. (%): C 48.27; H 4.59. Found (%): C 48.43; H 4.63.

EXAMPLE 19

Following the procedure of Example 17 using 34.0 g of 2-iodopropane in place of 12.8 g of dimethyl sulfate, there was obtained 30.2 g (yield: 78%) of isopropyl 2-acethylthiomethyl-3-(4-bromobenzoyl)-propionate as a colorless oil.

NMR (CDCl$_3$), ppm 1.25 (3H, d, J=7 Hz); 1.27 (3H, d, J=7 Hz); 2.34 (3H, s), 3.04–3.54 (5H, m); 5.03 (1H, heptet, J=7 Hz); 7.63 (2H, d, J=8 Hz); 7.84 (2H, d, J=8 Hz).

Elementary analysis for $C_{16}H_{19}BrO_4S$. Calcd. (%): C 49.62; H 4.94. Found (%): C 49.65; H 4.94.

EXAMPLE 20

Following the procedure of Example 17 using 20.5 g of benzyl bromide in place of 12.8 g of dimethyl sulfate, there was obtained 37.0 g (yield: 85%) of benzyl 2-acetylthiomethyl-3-(4-bromobenzoyl)propionate.

m.p. 79°–80° C. (crystals recrystallized from a mixture of hexane and diethyl ether).

Elementary analysis for $C_{20}H_{19}BrO_4S$. Calcd. (%): C 55.18; H 4.40. Found (%): C 55.19; H 4.58.

What is claimed is:

1. Benzoylpropionic acid derivatives represented by the general formula

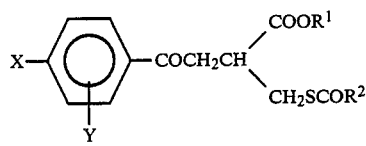

(wherein, $R^1$ represents a hydrogen atom, a lower alklyl group or a benzyl group, $R^2$ represents a lower alkyl or a phenyl group, X represents a hydrogen atom, a halogen atom, a lower alkyl group, a lower alkoxy group, a phenoxy group or a halogenophenoxy group, and Y represents a hydrogen atom or a lower alkyl group.

2. The benzoylpropionic acid derivatives as claimed in claim 1, wherein the lower alkyl group for $R^1$, $R^2$, X and Y are those containing up to 5 carbon atoms.

3. The benzoylpropionic acid derivatives as claimed in claim 1, wherein the lower alkoxy group for X are those containing up to 3 carbon atoms.

4. The benzoylpropionic acid derivatives as claimed in claim 1, wherein $R^1$ is a hydrogen atom, $R^2$ is a methyl group, X is a hydrogen atom, a bromine atom or a methyl group and Y is a hydrogen atom or a methyl group.

5. 2-acetylthiomethyl-3-benzoylpropionic acid.

6. 2-acetylthiomethyl-3-(4-bromobenzoyl)propionic acid.

* * * * *